United States Patent [19]

Haruta et al.

[11] Patent Number: 4,937,219
[45] Date of Patent: * Jun. 26, 1990

[54] ULTRA-FINE GOLD PARTICLE-IMMOBILIZED ALKALINE EARTH METAL COMPOUNDS AND METHODS FOR PRODUCTION THEREOF

[75] Inventors: Masatake Haruta, Kawanishi; Susumu Tsubota, Ashiya; Tetsuhiko Kobayashi; Yoshiko Nakahara, both of Ikeda, all of Japan

[73] Assignees: Agency of Industrial Science and Technology; Ministry of International Trade and Industry, both of Tokyo, Japan

[ * ] Notice: The portion of the term of this patent subsequent to Oct. 6, 2004 has been disclaimed.

[21] Appl. No.: 247,651

[22] Filed: Sep. 22, 1988

[30] Foreign Application Priority Data

Sep. 24, 1987 [JP] Japan ................... 62-240515

[51] Int. Cl.$^5$ .................. B01J 21/06; B01J 23/02; B01J 23/52; B01J 23/78
[52] U.S. Cl. .................... 502/174; 502/328; 502/340; 502/344
[58] Field of Search ............. 502/328, 340, 344, 174

[56] References Cited
FOREIGN PATENT DOCUMENTS 1472062 4/1977 United Kingdom ............. 502/243

Primary Examiner—W. J. Shine
Attorney, Agent, or Firm—Oblon, Spivak, McClelland, Maier & Neustadt

[57] ABSTRACT

An ultra-fine gold particle-immobilized alkaline earth metal compound having ultra-fine gold particles immobilized on an alkaline earth metal compound is useful as a catalyst or as an inflammable gas sensor. This compound is produced by (1) adding an aqueous solution of a gold compound dropwise to an aqueous solution containing an alkaline earth metal compound and having a pH value kept in the range of 7 to 11 thereby inducing immobilization of gold hydroxide on the compound, separating from the solution the gold hydroxide-immobilized compound, and calcining the separated compound at a temperature in the range of 80° to 800° C., (2) by adding a reducing agent to an aqueous solution of an alkaline earth metal having a gold compound dissolved therein, (3) by adding carbon dioxide gas or an acidic aqueous solution to an aqueous solution containing a gold compound and an alkaline earth metal compound thereby inducing immobilization of gold hydroxide on the alkaline earth metal compound, separating from the solution the gold hydroxide-immobilized compound, and calcining the separated compound at a temperature in the range of 100° to 800° C., or (4) by coprecipitating a gold compound and an alkaline earth metal and calcining the coprecipitate at a temperature in the range of 80° to 800° C.

30 Claims, 6 Drawing Sheets

ULTRA-FINE GOLD PARTICLE-IMMOBILIZED ALKALINE EARTH METAL COMPOUNDS AND METHODS FOR PRODUCTION THEREOF

BACKGROUND OF THE INVENTION

1. Field of the Invention

This invention relates to ultra-fine gold particle-immobilized alkaline earth metal compounds, methods for the production thereof, and oxidizing catalysts, reducing catalysts, and inflammable gas sensors each having the ultra-fine gold particles immobilized with alkaline earth metal compounds as a substantially main component thereof.

2. Prior Art Statement

It has been known that ultra-fine gold particles having a particle diameter smaller than about 0.1 μm exhibit specific physical and chemical properties different from those of the ordinary coarse gold grains ("Ultra-fine Particles" published by Agne Publishing Center in 1986).

Generally, ultra-fine particles possess large surface energies, coagulate easily and are therefore hard to handle. Particularly, the ultra-fine particles of gold exhibit a strong binding property between the individual particles and tend to agglomerate as compared with the ultra-fine particles of other noble metals such as Pt and Pd. Therefore, the development of the methods to deposit and immobilize ultra-fine gold particles on a carrier in a uniformly dispersed state has been desired.

Generally, the surface reactivities of the carriers vary with their kind of compound. Therefore, the methods suitable for the immobilization of the ultra-fine gold particles on the carrier also vary with the kind of carrier to be used. The only known way for effecting the immobilization of the ultra-fine gold particles, is a method which is utilized for only a few compounds such as, for example, oxides of manganese, iron, cobalt, nickel, and copper. These compounds have been studied with respect to a catalytic property and various other properties (Japanese Patent Public Disclosure SHO No. 60(1985)-238148). This method, however, is not totally practicable because the conditions for the immobilization of the ultra-fine gold particles are complicated and the amount of gold used is large. A method which comprises immersing a carrier in an aqueous solution containing a soluble gold compound and precipitating gold hydroxide on the carrier through the hydrolysis of urea or acetamide has been known in the art (U.S. Pat. No. 4,698,324). However, this method necessitates elaborate control of the conditions for the precipitation of gold and, at the same time, suffers from a poor gold utilization efficiency. The inventors made a study with a view to developing practical ultra-fine gold particle-immobilized compounds and a method for the production of the compounds. They consequently invented ultra-fine gold particle-immobilized compounds using various metal oxides as carriers and several methods for the production thereof. They applied for a patent of this invention in the United States (U.S. patent application Ser. No. 07/171,810, now U.S. Pat. No. 4,839,327).

OBJECT AND SUMMARY OF THE INVENTION

The inventors, convinced that the practical utility of these ultra-fine gold particle-immobilized compounds would be enhanced by broadening the spectrum of kinds of carriers, continued their study.

As a result, they for the first time found a method for immobilizing ultra-fine gold particles on alkaline earth metal compounds and have demonstrated that the ultra-fine gold particle-immobilized alkaline earth metal compounds possess outstanding properties suitable for oxidizing catalysts, reducing catalysts, inflammable gas sensors, etc.

Specifically, this invention aims to provide ultra-fine gold particle-immobilized alkaline earth metal compounds, methods for the production thereof, and oxidizing catalysts, reducing catalysts and inflammable gas sensors indicated below:

(1) Ultra-fine gold particle-immobilized alkaline earth metal compounds having ultra-fine gold particles immobilized on alkaline earth metal compounds.

(2) A method for the production of ultra-fine gold particle-immobilized alkaline earth metal compounds, characterized by adding dropwise an aqueous solution of a gold compound to an aqueous suspension or solution containing an alkaline earth metal compound with a pH value kept in the range of 7 to 11 and subsequently calcining the metal compound at a temperature in the range of 80° to 800° C.

(3) A method for the production of ultra-fine gold particle-immobilized alkaline earth metal compounds, characterized by preparing an aqueous suspension or solution of an alkaline earth metal compound having a gold compound dissolved therein and having a pH value kept in the range of 7 to 11 and adding dropwise a reducing agent to the aqueous suspension or solution with the pH value maintained within the aforesaid range thereby causing ultra-fine gold particles to be precipitated on the metal compound.

(4) A method for the production of ultra-fine gold particle-immobilized alkaline earth metal compounds, characterized by preparing an aqueous suspension or solution of an alkaline earth metal compound having a gold compound dissolved therein and having a pH value kept above the level of 11, bubbling carbon dioxide gas in or adding an acidic aqueous solution dropwise to the aqueous suspension or solution thereby adjusting the pH value to a level in the range of 7 to 11, and thereafter calcining the metal compound at a temperature in the range of 80° to 800° C.

(5) A method for the production of ultra-fine gold particle-immobilized alkaline earth metal compounds, characterized by preparing a mixed aqueous solution of a gold compound and an alkaline earth metal compound, neutralizing the mixed aqueous solution with an alkaline aqueous solution thereby giving rise to a coprecipitate, and then calcining the coprecipitate at a temperature in the range of 80° to 800° C.

(6) Oxidizing catalysts mainly consisting of ultra-fine gold particle-immobilized alkaline earth metal compounds which are produced by immobilizing ultra-fine gold particles on alkaline earth metal compounds.

(7) Reducing catalysts mainly consisting of ultra-fine gold particle-immobilized alkaline earth metal compounds which are produced by immobilizing ultra-fine gold particles on alkaline earth metal compounds.

(8) Inflammable gas sensors mainly consisting of ultra-fine gold particle-immobilized alkaline earth metal compounds which are produced by immobilizing ultra-fine gold particles on alkaline earth metal compounds.

The above and other objects and features of the invention will become more apparent from the following detailed description with reference to the accompanying drawings.

DETAILED DESCRIPTION OF THE PREFERRED EMBODIMENTS

Figure 1:
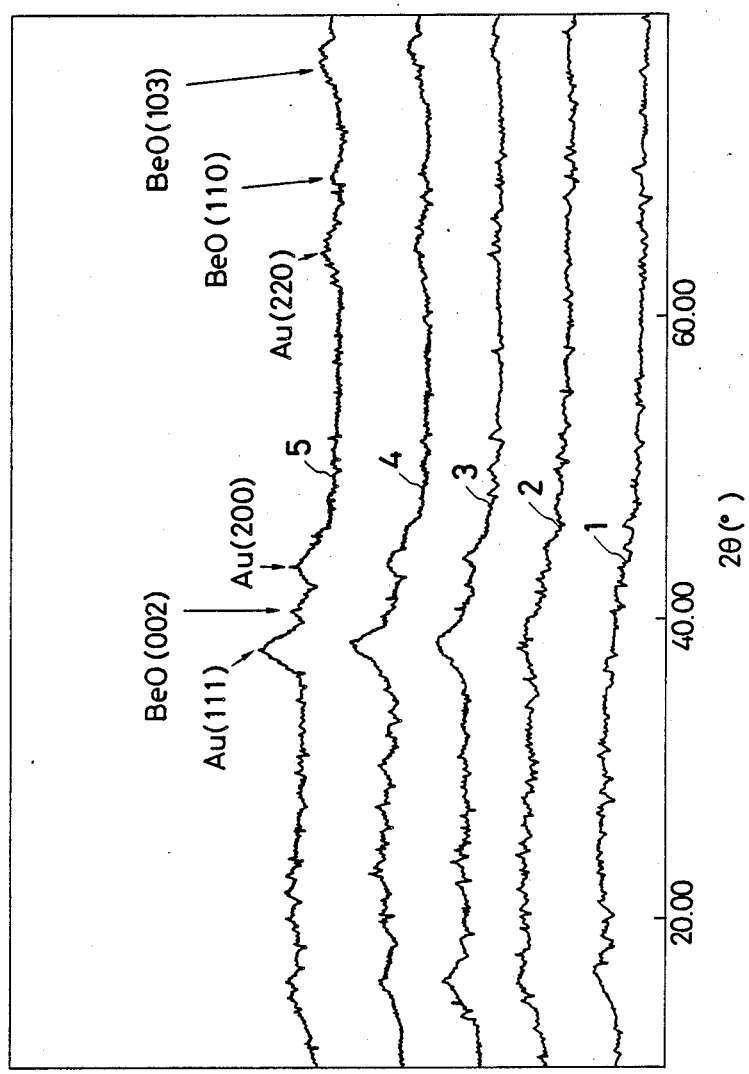
FIG. 1 is a graph showing the powder X-ray diffraction patterns of the sample obtained in Example 1.

First, the methods for production will be described.

The ultra-fine gold particle-immobilized alkaline earth metal compounds of the present invention can be produced by any of the following methods. The term "alkaline earth metal compounds" as used herein refers to oxides, hydroxides, carbonates, basic carbonates, nitrates, sulfates, and chlorides of beryllium, magnesium, calcium, strontium, and barium and further embraces composite oxides of these metals with other metals such as titanium, iron, cobalt, and nickel.

(I) First method:

This method accomplishes deposition and immobilization of ultra-fine gold particles on the surface of an alkaline earth metal compound by first preparing a suspension or solution having dispersed therein an alkaline earth metal compound as a carrier, keeping the solution adjusted to a pH value in the range of 7 to 11, preferably 7.5 to 10, and simultaneously stirred, adding dropwise the aqueous solution of a gold compound to the stirred solution thereby inducing adhesion of gold hydroxide to the alkaline earth metal compound, then separating from the suspension or solution the composite resulting from the adhesion of the gold hydroxide to the alkaline earth metal compound, and calcining the separated composite at a temperature in the range of 80° to 800° C. thereby inducing deposition of the ultra-fine gold particles onto the surface of the alkaline earth metal compound.

In the method, the alkaline earth metal compounds are required to possess solubilities in water as low as possible and, therefore, are desired to be the oxides, carbonates, basic carbonates, hydroxides, or sulfates of alkaline earth metals. Depending on the kind of alkaline earth metal to be used, the compounds may be suitably selected so as to fulfill the requirement that the solubility thereof in water should be low. Particularly desirably, these compounds are the ones produced by calcination at a high temperature so as to acquire improved crystallinity and a decreased specific surface area.

The alkaline earth metal compounds are not specifically restricted by their forms. In addition to the form of powder (which gives rise to a suspension when it is contained in water), these compounds may be prepared in various other forms as well. The alkaline earth metal compounds may also be used as supported on various carriers. Examples of usable carriers include foamed pieces, honeycombs, and pellets made of various ceramic materials as alumina, silica, titania, and magnesia and various metallic substances.

The amount of the alkaline earth metal compounds to be added to water is not particularly limited. Where these compounds are used in the form of powder, for example, the only requirement to the amount thereof is that the powder should be uniformly dispersed in water to produce a suspension. Usually, the amount is suitably selected in the approximate range of 10 to 200 g/lit. When these compounds are used in the form of shaped pieces, the only requirement to the amount thereof is that the shaped pieces should be thoroughly immersed in the resultant aqueous solution. In this case, therefore, the amount is not specifically limited.

For use in this invention, the compounds of gold are water-soluble gold salts. Examples of the gold compounds include chloroauric acid ($HAuCl_4$), sodium chloroaurate ($NaAuCl_4$), gold cyanide ($AuCN$), potassium gold cyanide $\{K[Au(CN)_2]\}$, and diethylamine-auric acid trichloride $[(C_2H_5)_2NH \cdot AuCl_3]$. The concentration of the water-soluble gold salt in the aqueous solution to be used for the dropwise addition is not specifically restricted. Suitably, this concentration is approximately in the range of 0.1 to 0.001 mol/lit.

For the control of pH value of the aqueous solution within the prescribed range, it generally suffices to use an alkali compound such as sodium carbonate, sodium hydroxide, potassium carbonate, or ammonia.

The aqueous solution of the gold compound must be gradually added dropwise and simultaneously stirred lest a sudden reaction should proceed and induce the precipitation of coarse gold hydroxide particles. Generally, the speed of the dropwise addition may be suitably selected, depending on the amount of the aqueous solution to be added, so that the dropwise addition will be completed in a period of about 3 to 60 minutes without inducing the precipitation of coarse hydroxide particles.

Suitably, the temperature of the aqueous solution containing the gold compound at the time of dropwise addition is approximately in the range of 20° to 80° C.

The amount of the gold compound to be added dropwise is determined by the amount of the ultra-fine gold particles required to be deposited. Though the amount thus deposited is variable with the kind, the form, and the specific surface area of the alkaline earth metal compounds to be used, it is generally in the range of about 0.1 to 42% by weight, preferably 5 to 40% by weight.

In the first method described above, since the gold compound is added gradually, even when the hydroxide of gold is formed in the solution phase during the dropwise addition, this gold hydroxide is immediately redissolved and the gold species resulting from this redissolution is adsorbed on the surface of the alkaline earth metal compound. Gold is precipitated as hydroxide selectively onto the surface of the alkaline earth metal compound, which acts as the nuclei for the precipitation. Thus, the gold compound added dropwise is not precipitated in the solution phase.

In the solution to which the gold compound has been added dropwise, the gold is generally present in the form of a complex ion possessing a negative electric charge. For the purpose of enhancing the efficiency in the selective precipitation of gold onto the surface of an alkaline earth metal compound, the pH value of the solution is desired to be adjusted to a level below the point of zero charge of the alkaline earth metal compound, namely, to a level to bring about the acid environment, so that the surface of the alkaline earth metal compound will possess a positive charge. When the pH value has to be adjusted to a level of the alkaline environment from the point of zero charge, the pH value should desirably be as close as possible to the point of zero charge. Preferably, the pH value should not exceed the pH value of the point of zero charge by more than 0.5. Thus, the alkaline earth metal compounds to be used are desired to possess a point of zero charge as high as possible. Generally, the alkaline earth metal compounds possessing a point of zero charge exceeding about pH 6 are easy to use.

Generally, gold is precipitated easily in the form of gold hydroxide onto the alkaline earth metal compound when the solution is in a state possessing a pH value approximately in the range of 7 to 11. At the time of this deposition-precipitation, the gold compounds tend to liberate acidic ions and lower the pH value of the solution. When $HAuCl_4$ is used as a gold compound, for example, it liberates $Cl^-$ ions and lowers the pH value of the solution. For the purpose of producing uniform deposit of ultra-fine gold particles, therefore, the variation of the pH value is desired to be controlled by dropwise addition of a suitable alkaline aqueous solution. Particularly when the solution of gold compound to be used has a low pH value on the order of about 7 to 8, the solution is desired to be added simultaneously with the alkaline aqueous solution lest the pH value should fall below 7.

When the alkaline earth metal compound on which the hydroxide of gold has been deposited as described above is calcined at a temperature in the range of 80° to 800° C., the deposited hydroxide of gold is decomposed into gold in the form of ultra-fine particles and strongly immobilized on the alkaline earth metal compound. Generally, the calcining time is suitably selected approximately in the range of 1 to 24 hours.

(II) Second method:

This method accomplishes immobilization of ultra-fine gold particles on the surface of an alkaline earth metal compound by preparing an aqueous suspension or solution of an alkaline earth metal compound having a gold compound dissolved therein and having a pH value adjusted to a level in the range of 7 to 11, preferably 7.5 to 10 and adding dropwise an aqueous solution of a reducing agent under agitation to the aqueous suspension or solution thereby causing gold to be reduced and deposited onto the surface of the alkaline earth metal compound.

The gold compounds, the alkaline earth metal compounds, and the alkali compounds to be used in this method may be identical to those used in the first method. The amount of the alkaline earth metal compounds to be added may be again identical to that in the first method. In the second method, the concentration of the gold compounds is suitably selected in the approximate range of $1 \times 10^{-2}$ to $1 \times 10^{-5}$ mol/liter. Suitably, the temperature of the aqueous suspension or solution of the alkaline earth metal compound is in the range of about 0° to 80° C.

Examples of reducing agents which are advantageously used herein include hydrazine, formalin, sodium citrate, diammonium citrate, and magnesium citrate. Suitably, the reducing agent is used in a concentration approximately ranging from $1 \times 10^{-1}$ to $1 \times 10^{-3}$ mol/liter. Properly, the aqueous solution of the reducing agent is added in an amount approximately 1.5 to 10 times the stoichiometrically required amount. The aqueous solution of the reducing agent must be added dropwise gradually lest the sudden precipitation of gold should occur in the solution. Generally, it suffices to carry out the dropwise addition at such a rate that it will be completed in a period of about 3 to 60 minutes. In consequence of the dropwise addition of the aqueous solution of the reducing agent, the gold compound adsorbed on the surface of the alkaline earth metal compound is reduced to gold and caused to adhere strongly to the surface.

In the solution of a high pH value, the surface of the alkaline earth metal compound may be negatively charged. If the negative charge is unduly large, the efficiency in the adhesion of the gold compound becomes poor. Thus, the pH value of the solution is desired to be as low as possible in the range of 7 to 11 so that the surface of the alkaline earth metal compound will be positively charged. If the surface has to be negatively charged, the amount of charge should be sufficiently small. When the solution is used at a pH value approximately in the range of 7 to 8, the alkaline aqueous solution is desired to be added dropwise simultaneously with the reducing agent so as to prevent the pH value of the aqueous solution from falling below the prescribed level and keep the speed of reduction and precipitation of gold substantially constant.

After the ultra-fine gold particles have been immobilized, the resultant composite is desired to be gradually calcined at a temperature above 80° C. so that the alkaline earth metal compound as a carrier will become porous to give a large specific surface area due to the vaporization of the adsorbed water.

When the ultra-fine gold particle-immobilized compound is expected to be used at a high temperature, the compound is desired to be heated in advance of actual use in the neighborhood of the working temperature so as to ensure the retention of stability at the high temperature.

(III) Third method:

This method accomplishes the immobilization of ultra-fine gold particles on the surface of an alkaline earth metal compound by preparing an aqueous suspension or solution of an alkaline earth metal compound having a gold compound dissolved therein and having a pH value kept above 11, preferably in the range of 11 to 12, bubbling carbon dioxide gas into the solution or gradually adding an acidic aqueous solution dropwise under agitation thereby lowering the pH value of the solution to a level in the range of 7 to 11 to precipitate gold in the form of gold hydroxide onto the surface of the alkaline earth metal compound, separating from the solution the composite covered with the gold hydroxide and calcining the separated composite at a temperature in the range of 80° to 800° C. thereby inducing the deposition of the ultra-fine gold particles.

The kinds and the amounts to be used of the gold compound, the alkaline earth metal compounds, and the alkaline aqueous solutions may be identical to those used in the first method. Suitably, the temperature of the solution containing the alkaline earth metal compound is approximately in the range of 20° to 80° C.

In this method, the gold compound is required to be contained in an aqueous suspension or solution of the alkaline earth metal compound in such a state that it will remain dissolved therein in the form of a complex ion having hydroxyl groups excessively bonded thereto. Depending on the particular kind of gold compound to be used, the pH value of the solution is adjusted so that, at a pH value exceeding 11, the gold compound will be dissolved in the form of a hydroxyl group-coordinated complex ion.

By bubbling carbon dioxide gas in or gradually adding an acidic aqueous solution dropwise to the solution prepared in the state described above, the pH value of the solution is gradually lowered to a level in the range of 7 to 11 and the gold is precipitated in the form of gold hydroxide onto the alkaline earth metal compound being nucleated by its surface.

The bubbling speed of carbon dioxide gas is not particularly restricted. The only requirement is that carbon dioxide gas should be bubbled uniformly throughout the aqueous solution.

The acidic aqueous solution for use of the dropwise addition may be an aqueous solution of nitric acid, hydrochloric acid, sulfuric acid, or acetic acid, for example. Though the concentration of this acidic aqueous solution is not particularly limited, the solution can be used easily in a concentration approximately in the range of $1 \times 10^{-1}$ to $1 \times 10^{-3}$ mol/liter. The amount of the acidic aqueous solution to be added dropwise may be suitably selected in the range in which the pH value of the aqueous solution of the alkaline earth metal compound will not fall below 7. Suitably, the speed of the dropwise addition is selected so that the addition will be completed in a period of about 3 to 60 minutes without inducing precipitation of coarse gold hydroxide particles in the solution phase.

When the composite resulting from the adhesion of the hydroxide of gold to the alkaline earth metal compound is calcined at a temperature in the range of 80° to 800° C., the adhering gold hydroxide is decomposed into ultra-fine gold particles uniformly dispersed and strongly immobilized. Suitably, the calcination time is generally selected approximately in the range of 1 to 24 hours.

When such an alkaline earth metal compound as magnesium carbonate or strontium hydroxide which is relatively soluble in water is used, the third method enjoys the advantage that the amount of dissolution can be decreased because the solution can be effectively operated at a high pH value.

In any of the first to third methods described above, the solution is desired to be stirred for a period of about 30 minutes to two hours after completion of the dropwise addition or the bubbling so as to ensure thorough adhesion of the gold compound to the alkaline earth metal compound.

When the precipitation of the hydroxide of gold is attained by the first method or the third method, there is a possibility that part of the gold compound still remains in the solution. In this case, the second method may be employed subsequently.

(IV) Fourth method:

This method accomplishes precipitation and immobilization of ultra-fine gold particles on the surface of an alkaline earth metal compound by preparing an aqueous solution of an alkaline earth metal compound and a gold compound, neutralizing the aqueous solution with an aqueous solution of an alkaline compound thereby inducing coprecipitation of the alkaline earth metal compound with gold hydroxide, and calcining the coprecipitate at a temperature in the range of 80° to 800° C. thereby causing deposition of the ultra-fine gold particles.

In this method, the alkaline earth metal compound as a starting material is required to be soluble in water. Depending on the particular kind of alkaline earth metal compound to be used, a suitable water-soluble alkaline earth metal compound may be selected from among nitrate, chloride, sulfate, etc. of the alkaline earth metal. Particularly, nitrate, chloride, sulfate, etc. of beryllium are advantageously usable for this method because the hydroxides thereof produced by neutralization are readily precipitated owing to meager solubility.

The gold compounds to be used in this method may be identical to those used in the first method.

The method for coprecipitating the alkaline earth metal compound and the gold hydroxide through neutralization is not particularly restricted. This coprecipitation may be attained by gradually adding dropwise the aqueous solution of an alkaline compound to the mixed aqueous solution of the alkaline earth metal compound and the gold compound or by gradually adding dropwise an aqueous solution containing the alkaline earth metal compound and the gold compound to the aqueous solution of an alkaline compound. Desirably, however, the coprecipitation is attained by adding dropwise the mixed aqueous solution of the alkaline earth metal compound and the gold compound to the aqueous solution of an alkaline compound at a solution temperature approximately in the range of 0° to 100° C., preferably 50° to 80° C. and, after completion of the dropwise addition, stirring the resultant at a temperature in the aforementioned range for a period in the range of 30 to 90 minutes so as to age the produced coprecipitate.

The concentration of the alkaline earth metal compound in the mixed solution of the alkaline earth metal compound and the gold compound is desired to be approximately in the range of 0.01 to 1 mol/liter, preferably 0.05 to 0.2 mol/liter. The ratio of the gold compound to the alkaline earth metal compound, Au/alkaline earth metal compound (atomic ratio), is desired to be approximately in the range of 1/50 to 1/9, preferably 1/19 to 1/9.

Examples of the alkaline compound in the aqueous solution of an alkaline compound which is used effectively herein include sodium carbonate, sodium hydroxide, potassium carbonate, and ammonia. When any of these compounds is used, the hydroxide or carbonate of the alkaline earth metal is produced in the coprecipitate, depending on the particular kind of compound to be used. For the purpose of precipitating an alkaline earth metal in the form of other salt such as sulfate, a water-soluble compound capable of producing an anion species which forms insoluble alkaline earth metal salt, namely, $Na_2SO_4$ is used, for example. Optionally, the aqueous solution of such an alkaline compound as described above may be more alkalinized by the addition of NaOH, for example, so as to control the pH of the aqueous solution of an alkaline compound for dropwise addition.

The concentration of the aqueous solution of an alkaline compound may be on the same order as that of the alkaline earth metal compound in the aqueous solution thereof. Suitably, the amount of the aqueous solution of an alkaline compound to be used is approximately in the range of 1.1 to 1.5 times the stoichiometrically required amount with respect to the total amount of the alkaline earth metal compound and the gold compound.

When the mixture of the alkaline earth metal compound with the hydroxide of gold produced in consequence of the coprecipitation by neutralization is calcined at a temperature in the range of 80° to 800° C., the hydroxide of gold is decomposed into ultra-fine gold particles which are immobilized on the alkaline earth metal compound. When a beryllium compound is used as an alkaline earth metal compound, the coprecipitate is desired to be calcined at a temperature around 200° C. Suitably, the calcination time is generally in the range of 1 to 24 hours.

By any of the methods of this invention, ultra-fine gold particles having a uniform particle diameter smaller than about 500 Å can be immobilized on an alkaline earth metal compound. Particularly ultra-fine gold particles smaller than about 250 Å in diameter, which have been heretofore unattainable, can be uniformly and strongly deposited. When the calcination temperature is kept below about 200° C., the ultra-fine gold particles so deposited can be obtained as extremely fine particles with a diameter smaller than 100 Å. These ultra-fine gold particles can be deposited in a ratio in the range of 0.1 to 42% by weight, preferably 5 to 40% by weight, on the alkaline earth metal compound by any of the four methods of this invention described above.

In any of the first to third methods described above, the alkaline earth metal compound can be used either in a premolded form or in a form supported on any of various carriers in addition to being used in the form of powder. For example, the ultra-fine gold particles can be immobilized directly on a sintered body having a platinum wire embedded there in or on a sintered body serving as an electrode having an electric lead connected thereto. By the first to the third methods, since the alkaline earth metal compound being used therein is dissolved sparingly, the ultra-fine gold particles can be precipitated directly on the alkaline earth metal compound. There are some cases nevertheless where the surface part of the alkaline earth metal compound is partially dissolved into the ambient solution and, depending on the particular kind of alkaline compound to be used, hydroxide or carbonate may be formed on the surface of the alkaline earth metal compound.

Where the ultra-fine gold particle-immobilized alkaline earth metal compound is to be obtained by the fourth method of this invention, the alkaline earth metal compound is in the form of hydroxide, carbonate, or some other salt, depending on the particular kind of the alkaline compound to be used for the formation of the coprecipitate.

In any of the first to fourth methods of this invention, when the ultra-fine gold particle-immobilized alkaline earth metal compound is calcined at a temperature above the decomposition temperature of the a alkaline earth metal compound in the presence of an oxygen-containing gas such as air, the alkaline earth metal compound is generally transformed into the oxide.

The ultra-fine gold particle-immobilized alkaline earth metal compound which is obtained by the present invention is a product having ultra-fine gold particles uniformly deposited on an alkaline earth metal compound and finds utility in various applications.

For example, since the ultra-fine gold particle-immobilized compound of the present invention is capable of catalyzing the combustion of such fuels as hydrogen, carbon monoxide, methanol, and propane at relatively low temperatures below 300° C. in a wide range of concentrations, it is useful as an oxidation catalyst for various space heaters and cooking heaters of the catalyst combustion type. It can also be used as a waste gas cleaning catalyst for oil stoves, oil fan heaters, and gas fan heaters or as an air cleaning catalytic filter for air conditioners. It is further useful as a catalyst for the removal of solvents by oxidation in the coating industry or as a catalyst for cleaning industrial gaseous effluents.

When the ultra-fine gold particle-immobilized alkaline earth metal compound is to be used as an oxidizing catalyst, this compound is desired to contain gold therein in a ratio approximately in the range of 5 to 11 atomic %. Particularly when carbon monoxide is to be oxidized at a temperature below 0° C., the beryllium compound obtained by the coprecipitation in the fourth method or the magnesium compound obtained by using magnesium citrate as a reducing agent in the second method can be used to advantage after it has been calcined at a temperature around 200° C. in advance.

The ultra-fine gold particle-immobilized compound of the present invention can be used advantageously as a catalyst for the reduction of nitrogen oxides such as NO and $NO_2$ with hydrogen, carbon monoxide, etc.

Furthermore, since the ultra-fine gold particle-immobilized alkaline earth metal compound of this invention exhibits an extremely high activity in oxidation catalysis even at relatively low temperatures around room temperature, it can be utilized as a sensor for such inflammable gases as hydrogen, carbon monoxide, methanol, and hydrocarbons. One method of producing an inflammable gas sensor is to coat a coiled platinum wire with, for example, a granular sintered material formed from the ultra-fine gold particle-immobilized alkaline earth metal compound. It is also possible to form a thick layer of the ultra-fine gold particle-immobilized alkaline earth metal compound on a plate-like thermistor. When containing an inflammable gas air contacts this sensor, the inflammable gas is burnt on the surface of the sensor to generate heat of combustion. Where the sensor used is produced by the former process, the combustion elevates the temperature of the platinum wire and increases the electric resistance thereof to permit detection of the inflammable gas. In the case of the sensor produced by the latter process the elevation of the temperature due to the combustion can be detected directly by the thermistor.

When the sensor carrier is a composite oxide of alkaline earth metal compound such as strontium titanate or barium titanate, for example, which exhibits semiconductivity, it can be utilized for the detection of an inflammable gas owing to the fact that its electric resistance varies by the surface adsorption or reaction of the inflammable gas.

By the present invention, the ultra-fine gold particles can be immobilized even on an alkaline earth metal compound which has heretofore been considered as impossible to deposit or immobilized ultra-fine gold particles thereon, and this immobilization can be effected quickly and efficiently on the aforementioned compound molded in various shapes.

The ultra-fine gold particle-immobilized alkaline earth metal compound which is obtained by this invention is highly useful as an oxidation catalyst, a reduction catalyst, an inflammable gas sensor, for example.

Further, since the ultra-fine gold particles can be directly immobilized on an alkaline earth metal compound which has been supported on a preformed sintered body or a carrier, they may be immobilized directly on a sensor element which has been produced by the conventional process and utilized readily for enhancing the performance of the sensor element.

Now, the present invention will be described more specifically below with reference to working examples.

EXAMPLE 1 (Fourth method)

To 3 liters of an aqueous solution containing 7 g of sodium carbonate per liter kept at 70° C. and stirred, 3 liters of a mixed aqueous solution containing 38.5 g of an aqueous solution containing 52% by weight of beryllium nitrate and 3.25 g of chloroauric acid tetrahydrate ($HAuCl_4 \cdot 4H_2O$) was added over a period of about 10 minutes. After completion of the addition, the resultant mixed solution was stirred at 70° C. for about two hours.

The precipitate consequently obtained from the mixed solution was separated by decantation, washed thoroughly with water, and filtered. The resultant residue was vacuum dried at 0° C. The powder consequently obtained was divided into five proportions. These proportions were calcined in air severally at 80° C., 150° C., 200° C., 400° C. and 500° C. for 15 hours to produce black powders containing Au at a ratio of 5 atomic % in all the metallic atoms present. The powder samples were analyzed by X-ray diffraction. The results are shown in FIG. 1. In the graph, the curves 1, 2, 3, 4, and 5 represent data obtained for the samples produced at calcination temperatures of 80° C., 150° C., 200° C., 400° C., and 500° C., respectively. From this X-ray diffraction graph, it is noted that gold was present in the sample powder in the metallic form. The particle diameters of the gold particles calculated from the half-value widths of peaks of the Au (111) planes were all found to fall in the range of 20 to 50 Å irrespective of the calcination temperature. From these data, it was indicated that gold was present in the form of extremely fine particles.

Furthermore, from the results of the powder X-ray diffraction, clear peaks of beryllium oxide, BeO, were recognized only in the samples which had been calcined at temperatures 400° C. and 500° C. From the results of thermogravimetric analysis, it was indicated that in the sample which had been calcined at 200° C., beryllium was present in the form of $Be(OH)_2$.

Figure 2:
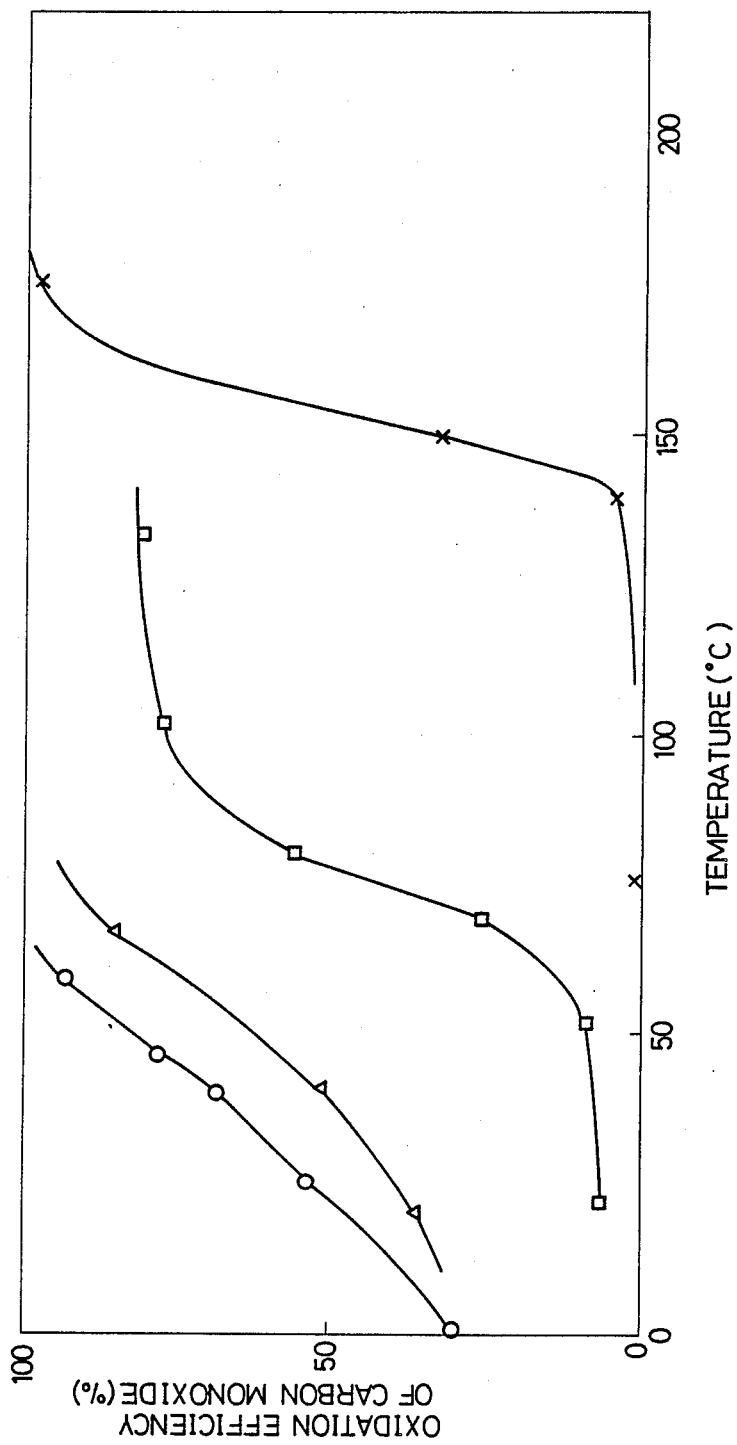
FIG. 2 is a graph showing the test results of the oxidation efficiency of carbon monoxide for the sample of Example 1.

The powder samples were sieved to obtain a 0.30-g fraction passed through 70 to 120 mesh. Air containing 1% by volume of carbon monoxide was passed through the fractions at a flow rate of 100 ml/minute to measure the activity of the sample powder for the oxidation of carbon monoxide. The results are shown in FIG. 2. In FIG. 2, the circular marks (o) represent the data obtained for the sample powder calcined at 80° C., the triangular marks (Δ) those obtained for the sample powder calcined at 150° C., the square marks (□) those obtained for the sample powder calcined at 400° C., and the crosses (x) those obtained for a conventional palladium catalyst supported on alumina. From the results shown above, it is noted that the ultra-fine gold particle-immobilized alkaline earth metal compound of this invention possesses an outstanding activity in catalyzing oxidation.

EXAMPLE 2 (Fourth method)

Coprecipitates containing Au in various ratios of 1 atomic %, 2 atomic %, 5 atomic %, 11 atomic %, and 33 atomic % were obtained from mixed aqueous solutions of beryllium nitrate and chloroauric acid by following the procedure of Example 1, except that the amount of chloroauric acid was varied. These precipitates were calcined in air at 200° C. for 15 hours, to obtain a variety of ultra-fine gold particle-immobilized beryllium hydroxides.

Figure 3:
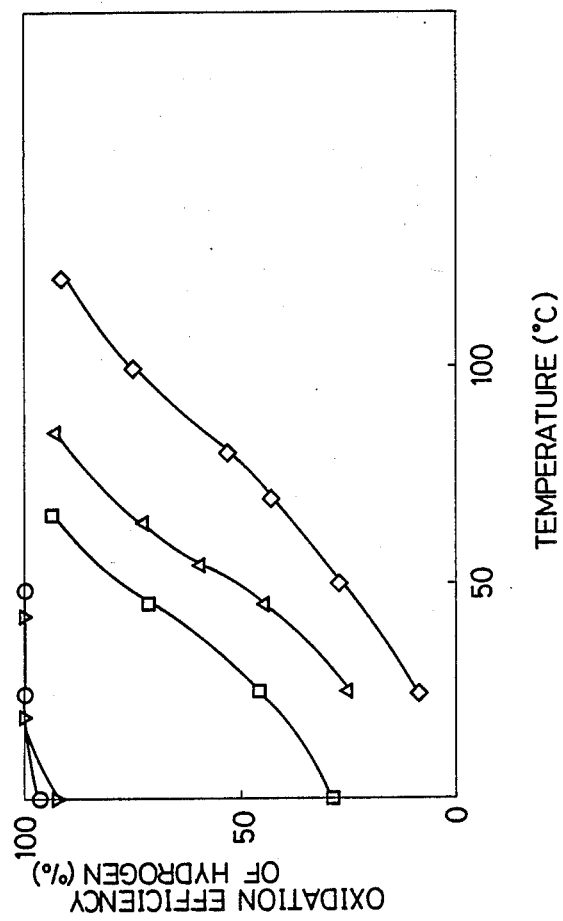
FIG. 3 is a graph showing the test results of the oxidation efficiency of hydrogen for the sample of Example 2.

These samples of ultra-fine gold particle-immobilized beryllium hydroxide were sieved to obtain a 0.3-g fraction passed through 70 to 120 mesh. Air containing 1% by volume of hydrogen was passed through the fractions at a flow rate of 100 ml/minute to measure the activity of the powder samples for the catalytic oxidation of hydrogen. The results are shown in FIG. 3. In the graph, the diamond marks (◇) represent the data of the sample containing Au in a ratio of 1 atomic %, the square marks (□) those of the sample containing Au in a ratio of 2 atomic %, the circular marks (o) those of the sample containing Au in a ratio of 5 atomic %, the inverted triangular marks (∇) those of the sample containing Au in a ratio of 11 atomic %, and the triangular marks (Δ) those of the sample containing Au in a ratio of 33 atomic %. It is noted from FIG. 3 that these species of ultra-fine gold particle-immobilized beryllium hydroxide exhibited high oxidation activity for hydrogen even at low temperatures below 100° C. The sample containing Au in a ratio of 5 atomic % and the sample containing Au in a ratio of 11 atomic % showed conversions close to 100% in the oxidation of hydrogen, indicating that they possessed exceptionally high catalytic activity.

Figure 4:
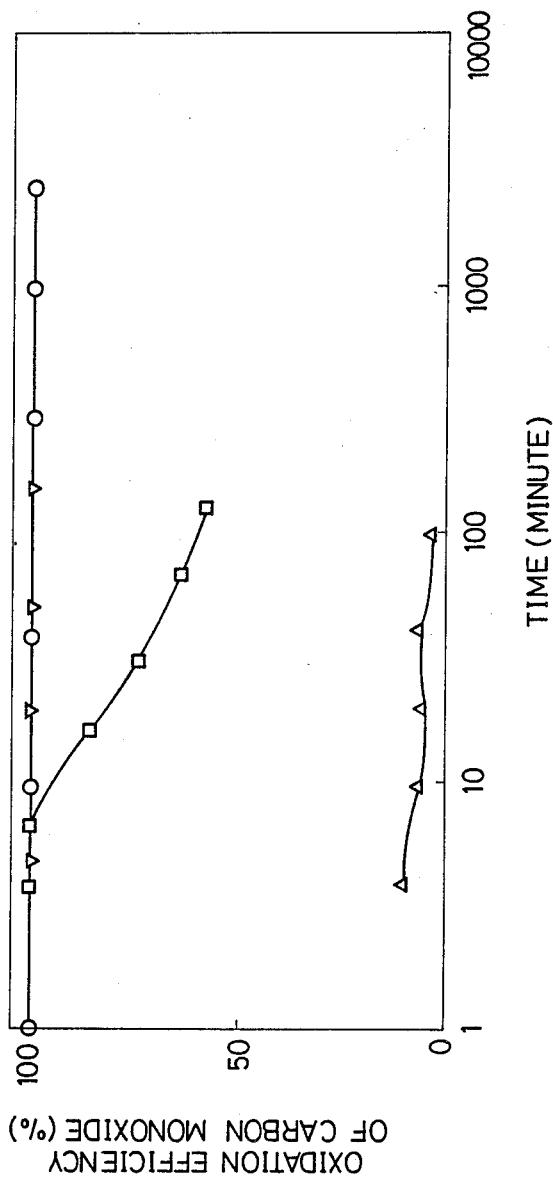
FIG. 4 is a graph showing the test results of the oxidation efficiency of carbon monoxide for the sample of Example 2.

By following the procedure of Example 1, the samples were also tested for the oxidation activity of carbon monoxide at a reaction temperature of −70° C. and for the change in the activity during use. The results are shown in FIG. 4. In the graph, the square marks (□) represent the data obtained for the sample containing Au in a ratio of 2 atomic %, the circular marks (o) those of the sample containing Au in a ratio of 5 atomic %, the inversed triangular marks (∇) those of the sample containing Au in a ratio of 11 atomic %, and the triangular marks (Δ) those of the sample containing Au in a ratio of 33 atomic %. It is noted from FIG. 4 that the beryllium hydroxide containing Au in a ratio of 5 atomic % and the beryllium hydroxide containing Au in a ratio of 11 atomic % could oxidize carbon monoxide in 100% efficiency even at such a low temperature as −70° C. for a long time. These results indicate that the ultra-fine gold particle-immobilized beryllium hydroxide containing gold in ratios of the range mentioned above can serve as highly desirable oxidation catalysts.

EXAMPLE 3 (First method)

In 50 ml of water, 5.0 g of beryllium oxide (BeO) powder was suspended. Since beryllium oxide was partially dissolved, the pH value of the suspension became 9.6. To this suspension, 100 ml of an aqueous solution containing $10^{-3}$ M of potassium chloroaurate ($KAuCl_4$) was gradually added dropwise over a period of 10 minutes. During the course of the dropwise addition, the pH of the solution was maintained in the range of 8 to 9. After completion of the dropwise addition, the suspension was kept stirred for one hour to induce precipitation of gold hydroxide (III) [$Au(OH)_3$] onto the surface of the beryllium oxide. When the colorless transparent supernatant was adjusted to pH 12 by adding sodium hydroxide, heated to 80° C., and admixed with formalin, the coloration of the supernatant in bluish purple due to the formation of collidal gold was very slight. The results indicate that the greater part of the complex ion of gold in the suspension was precipitated onto the surface of beryllium oxide. The beryllium oxide was washed with water, vacuum dried, and then calcined in air at 300° C. for three hours to effect thermal decomposition of gold hydroxide and consequent immobilization of gold on the surface of beryllium oxide. As a result, there was obtained beryllium oxide having gold carried thereon in a ratio of 1% by weight. By X-ray photoelectron spectrometry and the X-ray diffraction, the gold immobilized on the beryllium oxide was confirmed to be in a metallic state and to possess a particle diameter smaller than 100 Å.

When this ultra-fine gold particle-immobilized beryllium oxide was tested for oxidation activity of carbon monoxide in the same manner as in Example 1, the oxidation efficiency at 180° C. was found to be 35%.

EXAMPLE 4 (Second method)

In 167 ml of an aqueous solution containing $2.52 \times 10^{-2}$ M chloroauric acid, 2.0 g of beryllium oxide (BeO) powder was suspended. The pH value of the resultant aqueous suspension was changed from 2.8 to 9 by adding an aqueous sodium carbonate solution. To the aqueous solution which was heated at 40° C. and kept stirred, 126 ml of an aqueous 0.1 M diammonium citrate was gradually added dropwise over a period of 30 minutes with the pH value of the aqueous solution maintained in the range of 9 to 10, to induce deposition-reduction of gold on the surface of beryllium oxide. After the completion of the reducing reaction was confirmed by the change in the color of the aqueous solution from a transparent yellow to a colorless transparency, the beryllium oxide powder having gold carried thereon was separated from the aqueous solution by filtration and then thoroughly washed with water. The washed powder was calcined in air at 200° C. for 15 hours, to produce an ultra-fine gold particle-immobilized beryllium oxide (atomic ratio of Au/Be=1/19). From the half-value widths of the peaks of the X-ray diffraction of Au (111) plane, the gold particles were estimated to possess a diameter of about 300 Å. When the ultra-fine gold particle-immobilized beryllium oxide was tested for oxidation activity of carbon monoxide in the same manner as in Example 1, the oxidation efficiency at 180° C. was found to be 50%.

EXAMPLE 5 (Second method)

In 1,000 ml of an aqueous solution of $1 \times 10^{-2}$ M of chloroauric acid, 20 g of magnesium oxide (MgO) powder was suspended. The resultant suspension was adjusted to about pH 10, stirred at 80° C. for three hours, and then left standing at normal room temperature. To the stirred aqueous suspension, 2.5 ml of an aqueous solution of 3.7% by weight of formalin was added dropwise to effect deposition-reduction of gold on the surface of the magnesium oxide. The magnesium oxide powder having gold deposited thereon was separated from the aqueous solution by filtration and then washed thoroughly with water. The washed powder was divided into five portions. The five portions were calcined in air at various temperatures of 150° C., 180° C., 200° C., 250° C., 300° C., for five hours to produce ultra-fine gold particle-immobilized magnesium oxides each having 10% by weight of gold immobilized thereon (atomic ratio of Au/Mg=1/38).

Figure 5:
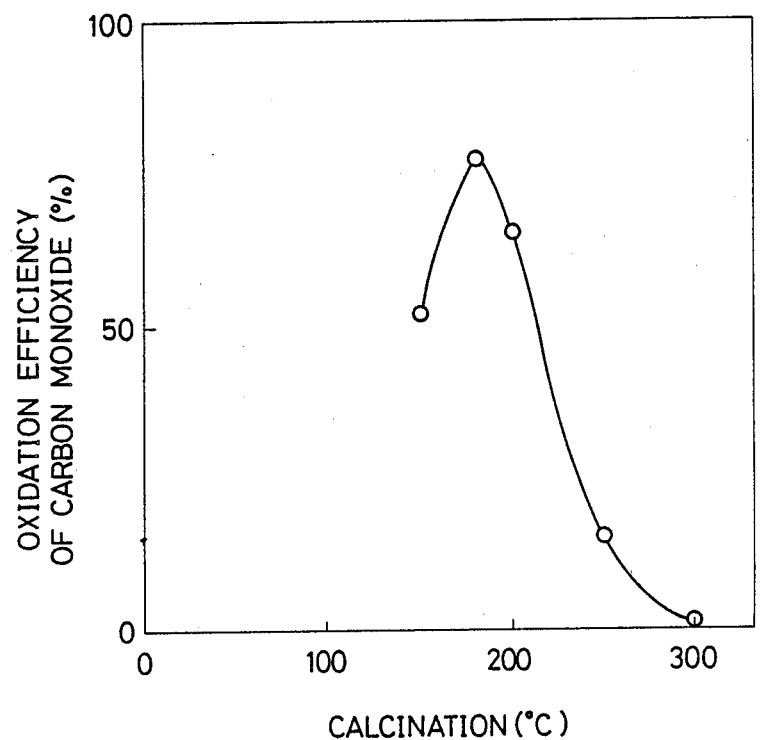
FIG. 5 is a graph showing the test results of the oxidation efficiency of carbon monoxide for the sample of Example 5.

These ultra-fine gold particle-immobilized magnesium oxides were sieved to obtain a 0.20 g fraction passed through 120 to 200 mesh. Air containing 1% by volume of carbon monoxide was passed through the fraction at a flow rate of 67 ml/min and at $-70°$ C. for 100 minutes. After the 100 minutes' passage of the mixed air, the fractions were tested for oxidation efficiency of carbon monoxide. The results are shown in FIG. 5. The conversions of CO by oxidation were above 50% when the calcination temperature was in the range of 150° to 200° C., clearly indicating that these showed very high catalytic activity at low temperatures.

EXAMPLE 6 (Second method)

In 100 ml of an aqueous solution of $2.5 \times 10^{-2}$ M chloroauric acid, 2.0 g of magnesium oxide (MgO) powder was suspended. To the resultant suspension which was adjusted to about pH 11 and kept stirred at 0° C., 100 ml of aqueous solution of 0.1 g of diammonium citrate was added dropwise to induce deposition-reduction of gold on the surface of the magnesium oxide. The magnesium oxide having gold deposited thereon was washed with water and then treated in the same manner as in Example 5. Then, for the purpose of enabling the magnesium oxide to form micropores therein, it was calcined in air at 200° C. for three hours. Consequently, there was produced magnesium oxide having 2.5% by weight of gold immobilized thereon (atomic ratio of Au/Mg=1/152).

EXAMPLE 7 (First method)

To 100 ml of an aqueous solution having 5.2 g of basic magnesium carbonate $(3MgCO_3 \cdot Mg(OH)_2 \cdot 3H_2O)$ suspended therein and kept at 80° C., 100 ml of an aqueous solution of $3 \times 10^{-2}$ chloroauric acid was added over a period of 20 minutes. At the end of the addition, the resultant mixed solution had a pH value of 8.5. The mixed solution was left aging at an elevated temperature for three hours. The composite resulting from the aging was separated from the solution by filtration. The basic magnesium carbonate powder having gold hydroxide deposited thereon consequently obtained was washed repeatedly with water. The washed powder was calcined at 300° C. for five hours, to produce an ultra-fine gold particle-immobilized basic magnesium carbonate (atomic ratio of Au/Mg=1/19).

EXAMPLE 8 (Second method)

In 1,000 ml of water, 10 g of granular pellets of magnesium oxide (MgO) 4 mm in particle diameter were suspended. Since the surface of magnesium oxide was partly dissolved in the suspension, the pH value of the suspension was 10.8. This suspension was heated to 70° C. To the heated suspension, 500 ml of an aqueous solution of $1 \times 10^{-2}$ M of diethylamine auric acid trichloride $[(C_2H_5)_2NH \cdot Au]Cl_3$ was gradually added dropwise over a period of three minutes. At the end of the dropwise addition, the pH value of the resultant mixed solution was 9.8. After the dropwise addition was completed, the suspension was stirred for one hour, to form nucleus for the crystallization of gold hydroxide (III) $[Au(OH)_3]$ on the granular pellets of magnesium oxide. Since the complex ion of gold still remained in a large portion in the suspension at this stage, the suspension was cooled to 0° C. and 400 ml of an aqueous solution containing 0.50 g of hydrazine hydrochloride was gradually added dropwise thereto, to induce deposition-reduction of gold on the granular pellets of magnesium oxide. The supernatant of the suspension after completion of the deposition-reduction was colorless and transparent. When it was adjusted to pH 12 by adding sodium hydroxide, heated to 80° C., and then admixed with formalin, it showed absolutely no change of color due to the reduction of gold. The results indicate that all the remaining complex ion of gold in the suspension was precipitated on the surface of the granular pellets of magnesium oxide. The magnesium oxide pellets were washed with water, dried at 120° C., and further calcined in air at 200° C. for 10 hours, to induce immobilization of gold on the granular pellets of magnesium oxide and consequently produce catalytic Au (10% by weight)/MgO granular pellets (atomic ratio of Au/Mg=1/19).

By X-ray photoelectron spectroscopy and X-ray diffraction, it was confirmed that the gold deposited on the surface of the catalyst was in a metallic state and had a particle diameter around 100 Å and that part of MgO had been transformed into $Mg(OH)_2$.

EXAMPLE 9 (Second method)

In 30 ml of an aqueous solution containing 0.215 g of chloroauric acid tetrahydrate and kept at 50° C., 1.0 g of magnesium oxide powder was dispersed. The resultant aqueous dispersion which had a pH value of 9.2 was kept stirred and 50 ml of an aqueous solution containing 0.9 g of magnesium citrate was added dropwise thereto over a period of one hour. The supernatant was discarded and the magnesium oxide having gold deposited thereon by reduction was washed with distilled water several times, and vacuum dried overnight. The dried magnesium oxide was calcined in air at 200° C. for 26 hours inside an electric furnace, to produce a catalytic Au(10% by weight)/MgO (atomic ratio of Au/Mg=1/19).

EXAMPLE 10 (Second method)

In 250 ml of an aqueous solution of $1 \times 10^{-2}$ M of gold potassium cyanide $\{K[Au(CN)_2]\}$, 5 g of magnesium oxide powder was suspended. The resultant suspension was adjusted to pH 11, stirred at 80° C. for three hours, and then left standing at room temperature. This suspension was kept stirred and 100 ml of an aqueous solution of 3% by weight of hydrazine was added dropwise thereto at 0° C. over a period of 20 minutes to induce deposition-reduction of gold on the surface of magnesium oxide. The deposited magnesium oxide was separated by filtration from the solution, washed with water, and calcined in air at 200° C. for 15 hours, to produce magnesium oxide having 10% by weight of gold deposited thereon (atomic ratio of Au/Mg=1/38)

EXAMPLE 11 (Test for catalytic activity for oxidation)

The ultra-fine gold particle-immobilized alkaline earth metal compounds obtained in Examples 6 to 10 were tested for oxidation activity of carbon monoxide at 0° C. in the same manner as in Example 5. The oxidation efficiencies for carbon monoxide, determined after 100 minutes' passage of the reaction gas, were 90% in the case of the compound of Example 6, 54% in the case of the compound of Example 7, 86% in the case of the compound of Example 8, 100% in the case of the compound of Example 9, and 23% in the case of the compound of Example 10. The magnesium oxide of Example 9 showed a conversion exceeding 70% even after 2,000 minutes' run at a reaction temperature of −70° C.

From these results, it is noted that the ultra-fine gold particle-immobilized magnesium oxide of the present invention possesses a highly satisfactory activity in catalytic oxidation as compared with the conventional palladium based catalysts which catalyze oxidation of carbon monoxide only at temperatures above 150° C.

EXAMPLE 12 (Second method)

A honeycomb carrier of cordiellite $15 \times 15 \times 2$ cm (containing 200 cells/square inch) was impregnated with magnesium nitrate and calcined at 800° C. for four hours, to obtain a honeycomb having 15% by weight of MgO deposited thereon.

This honeycomb was immersed in 1 liter of an aqueous solution containing 9.7 g of chloroauric acid tetrahydrate and adjusted to pH 10.2. The solution was kept stirred and 500 ml of an aqueous solution saturated with magnesium citrate was added dropwise thereto over a period of 30 minutes. Then, the resultant mixed solution was stirred for one hour.

The solution and the honeycomb were separated from each other. The solution was adjusted to pH 12 by addition of sodium hydroxide and then admixed with formalin at 80° C., to induce no precipitation of gold. The results indicate that all the gold in the solution was deposited on the honeycomb.

The honeycomb separated from the aqueous solution was washed with water and dried in an electric furnace at 120° C. When air containing 1% by volume of carbon monoxide was passed through the dry honeycomb at a space velocity of $1 \times 10^4 h^{-1}$ at room temperature, 91% of the carbon monoxide was oxidized into carbon dioxide.

EXAMPLE 13 (Second method)

In 100 ml of an aqueous solution of hydrochloric acid containing $1 \times 10^{-2}$ M of chloroauric acid, 2.0 g of calcium hydroxide powder was suspended and adjusted to pH 11, stirred at 80° C. for three hours, and then left standing at normal room temperature for five hours. Thereafter, the resultant suspension was kept stirred and 100 ml of an aqueous solution of 3% by weight of formalin was added dropwise thereto over a period of 30 minutes to induce precipitation of gold on the surface of calcium hydroxide.

Then, the precipitated calcium hydroxide was separated from the solution by filtration, washed with water, and then calcined in air at 200° C. for 15 hours, to produce calcium hydroxide having 10% by weight of gold deposited thereon (atomic ratio of Au/Ca=1/27).

EXAMPLE 14 (Second method)

In 100 ml of an aqueous solution containing $1 \times 10^{-2}$ M of chloroauric acid, 2 g of strontium titanate powder was suspended. The resultant suspension was adjusted from pH 3.2 to pH 10.5 by addition of an aqueous sodium carbonate solution. The suspension was stirred at 80° C. for three hours and then left standing at normal room temperature for 10 hours. The resultant suspension was kept stirred and 100 ml of an aqueous solution containing 3% by weight of formalin was added dropwise thereto at room temperature over a period of one hour. Thereafter, the resultant mixed solution was left standing at 90° C. for about two hours to promote the reduction with formalin. The precipitate consequently formed was separated by filtration from the solution, washed with water, and then calcined in air at 200° C. for 15 hours, to produce hydrated strontium titanate having 10% by weight of gold deposited thereon.

EXAMPLE 15 (Second method)

In 1,000 ml of an aqueous solution of $1\times10^{-2}$ M of chloroauric acid, 20 g of barium titanate powder was suspended. The resultant suspension was adjusted from pH 2.29 to 10 by adding an aqueous sodium carbonate solution. The resultant suspension was stirred at 80° C. for three hours and then left standing at normal room temperature for 12 hours. This suspension was kept stirred and 500 ml of an aqueous solution of 3% by weight of formalin was added dropwise thereto over a period of 20 minutes, and the resultant mixed solution was left standing at 90° C. for three hours. The precipitate consequently formed was separated by filtration from the solution, washed with water, and calcined in air at 200° C. for 15 hours, to produce hydrated barium titanate having 10% by weight of gold deposited thereon.

EXAMPLE 16 (Test for catalytic activity for oxidation)

Figure 6:
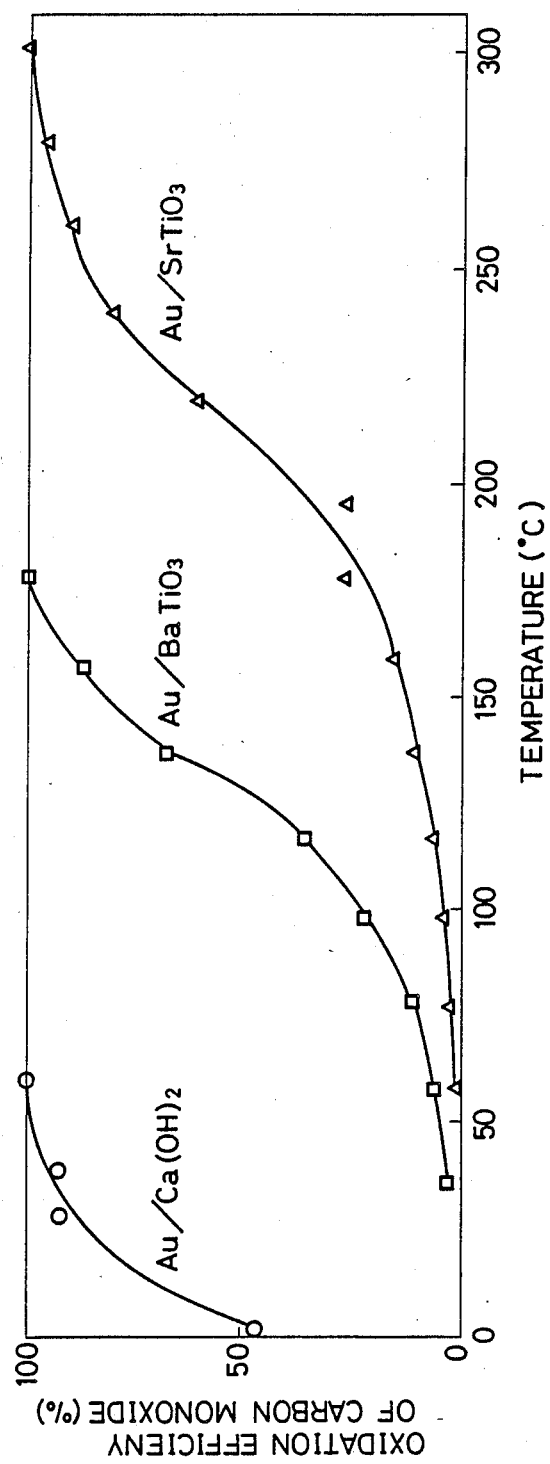
FIG. 6 is a graph showing the test results of the oxidation efficiency of carbon monoxide for the sample of Example 16.

The ultra-fine gold particle-immobilized alkaline earth metal compounds obtained in Examples 13 to 15 were tested for catalytic activity for the oxidation of carbon monoxide in the same manner as in Example 5. The results are shown in FIG. 6. In the graph, the circular marks (o) represent the data obtained for the compound of Example 13, the square marks (□) those for the compound of Example 14, and the triangular marks (Δ) those for the compound of Example 15. From FIG. 6, it is noted that the compounds of Examples 13 to 15 all possessed highly satisfactory activity in the oxidation of carbon monoxide.

EXAMPLE 17 (Third method)

In 100 ml of an aqueous solution of 0.1 M of sodium hydroxide, 5 g of strontium hydroxide was suspended. In the resultant suspension, 0.46 g of sodium chloroaurate was dissolved. When carbon dioxide gas was caused to bubble up the aqueous suspension of strontium oxide at 50° C. at a flow rate of 20 ml/minute, the pH value of the aqueous suspension gradually fell from 12.5 to 9.5. At this stage, the bubbling of $CO_2$ was discontinued and the suspension was stirred for two hours. Then, the suspension was cooled to 0° C. and kept stirred for 12 hours to induce precipitation of gold hydroxide on the strontium oxide particles.

The strontium oxide powder having gold hydroxide deposited thereon was separated from the solution, washed with water, and then vacuum dried overnight. The powder consequently obtained was calcined in air at 300° C., to produce an ultra-fine gold particle-immobilized strontium oxide. When this sample was tested for activity in catalyzing oxidation of carbon monoxide in the same manner as in Example 5, the conversion of carbon monoxide by oxidation at 150° C. was found to be 83%.

EXAMPLE 18 (Test for gas sensor performance)

The Au/Be (atomic ratio of Au/Be=1/19) type coprecipitate prepared by the method of Example 1 was calcined in air at 400° C. for 15 hours. The powder consequently obtained was transformed into a slurry by adding a small amount of water and finely ground in a mortar. The paste consequently obtained was applied on a platelike ceramic thermistor 5×10 mm in surface area to a thickness of about 0.5 mm. The coating of the paste was dried overnight at 120° C. and then calcined in air at 400° C. for three hours, to produce a catalytic combustion type gas sensor.

Detection of an inflammable gas was effected by measuring the difference in temperature between the thermistor coated with the Au-Be type catalyst which can consequently induce combustion of the inflammable gas and a thermistor not provided with any coating which cannot consequently induce combustion of the inflammable gas. When the difference in temperature between the two thermistors was measured at 150° C. by using air containing 1% by volume of carbon monoxide, it was found to be 8.2° C. This difference in temperature fell to 1.6° C. when the concentration of carbon monoxide was decreased to 0.1% by volume. The results show that the application of a thick film of an ultra-fine gold particle-immobilized alkaline earth metal compound on a thermistor leads to a catalytic combustion type gas sensor.

EXAMPLE 19 (Test for catalytic activity for reduction)

The catalysts obtained in Example 9 and Example 15 were tested for the catalytic activity in the reduction of nitrogen oxides. Argon gas containing 350 ppm of nitrogen monoxide and 5,000 ppm of carbon monoxide was passed through a bed packed with 0.3 g of catalyst powder sieved between 120 mesh and 200 mesh at a flow rate of 100 ml/minute, to measure the conversion of nitrogen monoxide by reduction with carbon monoxide at 150° C. The amount of nitrogen gas converted by the reduction of nitrogen monoxide was determined by gas chromatography. Thus, the conversion of nitrogen monoxide by reduction was found to be 100% in the case of the catalyst of Example 9 and 73% in the case of the catalyst of Example 15. From the results indicated above, it is noted that the ultra-fine gold particle-immobilized alkaline earth metal compounds produced by this invention serve as nitrogen oxide-reducing catalysts which function effectively even at low temperatures.

What is claimed is:

1. An ultra-fine gold particle-immobilized alkaline earth metal compound, comprising:
   ultra-fine gold particles immobilized on an alkaline earth metal compound which is at least one compound selected from the group consisting of oxides, hydroxides and basic carbonates severally of beryllium, magnesium, calcium, strontium and barium and composite oxides of one of beryllium, magnesium, calcium, strontium and barium with one of titanium, iron, cobalt and nickel.

2. The ultra-fine gold particle-immobilized alkaline earth metal compound according to claim 1, wherein the amount of said ultra-fine gold particles to be immobilized is in the range of 0.1 to 42% by weight based on the amount of said alkaline earth metal compound.

3. A method for the production of an ultra-fine gold particle-immobilized alkaline earth metal compound, which comprises the steps of adding an aqueous solution of a gold compound dropwise to an aqueous solution of an alkaline earth metal compound kept at a pH in the range of 7 to 11 thereby producing a solution of said alkaline earth metal compound having gold hydroxide immobilized thereon, separating from said solution said gold hydroxide-immobilized alkaline earth metal compound, and calcining the separated compound at a temperature in the range of 80° to 800° C.

4. The method according to claim 3, wherein said alkaline earth metal compound is at least one member selected from the group consisting of oxides, hydroxides, carbonates, basic carbonates, nitrates, sulfates, and chlorides severally of beryllium, magnesium, calcium, strontium, and barium, and composite oxides of titanium with said alkaline earth metals, iron with said alkaline earth metals, cobalt with said alkaline earth metals, and nickel with said alkaline earth metals.

5. The method according to claim 3, wherein said gold compound is at least one member selected from the group consisting of $HAuCl_4$, $NaAuCl_4$, $AuCN$, $K[Au(CN)_2]$ and $(C_2H_5)_2NH \cdot AuCl_3$.

6. The method according to claim 3, wherein said alkaline earth metal compound is suspended in said aqueous solution of alkaline earth metal compound and the content of said alkaline earth metal compound in said aqueous solution is in the range of 10 to 200 g/liter.

7. The method according to claim 3, wherein the concentration of said gold compound in said aqueous solution of gold compound for dropwise addition is in the range of 0.1 to 0.001 mol/liter.

8. The method according to claim 3, wherein said dropwise addition of the aqueous solution of gold compound is carried out while the temperature of said aqueous solution is kept in the range of 20° to 80° C.

9. A method for the production of an ultra-fine gold particle-immobilized alkaline earth metal compound, which comprises the steps of adding a reducing agent to an aqueous solution of an alkaline earth metal compound having a gold compound dissolved therein and having a pH value thereof kept in the range of 7 to 11 thereby producing a solution containing said alkaline earth metal compound having ultra-fine gold particles immobilized thereon and separating from said solution said alkaline earth metal compound having said ultra-fine gold particles immobilized thereon.

10. The method according to claim 9, wherein said alkaline earth metal compound is at least one member selected from the group consisting of oxides, hydroxides, carbonates, basic carbonates, nitrates, sulfates, and chlorides severally of beryllium, magnesium, calcium, strontium, and barium, and composite oxides of titanium with said alkaline earth metals, iron with said alkaline earth metals, cobalt with said alkaline earth metals, and nickel with said alkaline earth metals.

11. The method according to claim 9, wherein said gold compound is at least one member selected from the group consisting of $HAuCl_4$, $NaAuCl_4$, $AuCN$, $K[Au(CN)_2]$ and $(C_2H_5)_2NH \cdot AuCl_3$.

12. The method according to claim 9, wherein the concentration of said gold compound in said aqueous solution of alkaline earth metal compound is in the range of $1 \times 10^{-2}$ to $1 \times 10^{-5}$ mol.

13. The method according to claim 9, wherein said reducing agent is one member selected from the group consisting of hydrazine, formalin, sodium citrate, diammonium citrate, and magnesium citrate.

14. The method according to claim 9, wherein the temperature of said aqueous solution of alkaline earth metal compound is in the range of 0° to 80° C.

15. The method according to claim 9, wherein the amount of said reducing agent is approximately in the range of 1.5 to 10 times the amount stoichiometrically necessary for the reduction of gold.

16. A method for the production of an ultra-fine gold particle-immobilized alkaline earth metal compound, which comprises the steps of adding one member selected from the group consisting of carbon dioxide gas and acidic aqueous solutions to an aqueous solution of an alkaline earth metal compound having a gold compound dissolved therein and having a pH value kept above 11 thereby adjusting the pH value of said aqueous solution to a level in the range of 7 to 11 and producing a solution containing said alkaline earth metal compound having gold hydroxide deposited thereon, separating from said solution said alkaline earth metal compound having said gold hydroxide deposited thereon, and calcining the separated compound at a temperature in the range of 80° to 800° C.

17. The method according to claim 16, wherein said alkaline earth metal compound is at least one member selected from the group consisting of oxides, hydroxides, carbonates, basic carbonates, nitrates, sulfates, and chlorides severally of beryllium, magnesium, calcium, strontium, and barium, and composite oxides of titanium with said alkaline earth metals, iron with said alkaline earth metals, cobalt with said alkaline earth metals, and nickel with said alkaline earth metals.

18. The method according to claim 16, wherein said gold compound is at least one member selected from the group consisting of $HAuCl_4$, $NaAuCl_4$, $AuCN$, $K[Au(CN)_2]$ and $(C_2H_5)_2NH \cdot AuCl_3$.

19. The method according to claim 16, wherein the temperature of said aqueous solution of alkaline earth metal compound is in the range of 20° to 80° C.

20. The method according to claim 16, wherein said acidic aqueous solution is an aqueous solution of one member selected from the group consisting of nitric acid, hydrochloric acid, sulfuric acid, and acetic acid.

21. A method for the production of an ultra-fine gold particle-immobilized alkaline earth metal compound, which comprises the steps of neutralizing an aqueous solution having a gold compound and an alkaline earth metal compound dissolved therein with an alkaline aqueous solution thereby inducing coprecipitation of said gold compound and said alkaline earth metal compound, separating the resultant coprecipitate from said aqueous solution, and calcining the separated coprecipitate at a temperature in the range of 80° to 800° C.

22. The method according to claim 21, wherein said alkaline earth metal compound is soluble in water.

23. The method according to claim 21, wherein said alkaline earth metal compound is one member selected from the group consisting of nitrates, chlorides, and sulfates of alkaline earth metals.

24. The method according to claim 21, wherein said alkaline earth metal is beryllium.

25. The method according to claim 21, wherein said gold compound is at least one member selected from the group consisting of $HAuCl_4$, $NaAuCl_4$, $AuCN$, $K[Au(CN)_2]$ and $(C_2H_5)_2NH \cdot AuCl_3$.

26. The method according to claim 21, wherein the concentration of alkaline earth metal compound in said aqueous solution having said gold compound and said alkaline earth metal compound dissolved therein is in the range of 0.01 to 1 mol/liter.

27. The method according to claim 21, wherein the ratio of said gold compound to said alkaline earth metal compound in said aqueous solution having said gold compound and said alkaline earth metal compound dissolved therein is in the range of 1/50 to 1/9 in terms of the atomic ratio of gold to alkaline earth metal.

28. A catalyst containing as a substantial component thereof an ultra-fine gold particle-immobilized alkaline earth metal compound having ultra-fine gold particles immobilized on an alkaline earth metal compound selected from the group consisting of oxides, hydroxides and basic carbonates severally of beryllium, magnesium, calcium, strontium and barium and at least one composite oxide of one of beryllium, magnesium, calcium, strontium and barium with one of titanium, iron, cobalt and nickel.

29. The catalyst according to claim 28, wherein said catalyst is used for oxidation.

30. The catalyst according to claim 29, wherein said catalyst is used for reduction.

* * * * *